United States Patent [19]

Wasley

[11] Patent Number: 4,960,787
[45] Date of Patent: Oct. 2, 1990

[54] CERTAIN PYRROLYL-SUBSTITUTED HYDROXAMIC ACID DERIVATIVES

[75] Inventor: Jan W. F. Wasley, Chatham, N.J.

[73] Assignee: Ciba-Geigy Corporation, Ardsley, N.Y.

[21] Appl. No.: 306,975

[22] Filed: Feb. 6, 1989

[51] Int. Cl.$^5$ .................... A61K 31/40; C07D 207/34; C07D 207/337
[52] U.S. Cl. .................................. 514/423; 514/427; 548/537; 548/561
[58] Field of Search ................. 548/537, 561; 514/423, 514/427

[56] References Cited

U.S. PATENT DOCUMENTS

| | | | |
|---|---|---|---|
| 3,952,012 | 4/1976 | Carson | 548/561 |
| 4,769,387 | 9/1988 | Summers et al. | 514/468 |
| 4,782,085 | 11/1988 | Varma et al. | 514/507 |
| 4,792,560 | 12/1988 | Huang | 514/311 |

FOREIGN PATENT DOCUMENTS

| | | |
|---|---|---|
| 196184 | 10/1986 | European Pat. Off. . |
| 199151 | 10/1986 | European Pat. Off. . |
| 248594 | 12/1987 | European Pat. Off. . |
| 273451 | 7/1988 | European Pat. Off. . |
| 279263 | 8/1988 | European Pat. Off. . |
| 279281 | 8/1988 | European Pat. Off. . |
| 292699 | 11/1988 | European Pat. Off. . |
| 320628 | 6/1989 | European Pat. Off. . |

OTHER PUBLICATIONS

Argentieri FASEB J. 2(4) A369 (1988).
Summers et al., J. Med. Chem. vol. 30 pp. 574–580 (1987).
Artico et al., J. Med. Chem. vol. 31 pp. 802–806 (1988).
Jackson J. Med. Chem. vol. 31, No. 3 pp. 499 (1988).
Reynolds, Biochemical Pharmacology vol. 37 No. 23 pp. 4531–4537 (1988).
Summers et al., J. Med. Chem. vol. 31 pp. 1960–1964 (1988).

Primary Examiner—Mark L. Berch
Attorney, Agent, or Firm—Norbert Gruenfeld

[57] ABSTRACT

The invention relates to the pyrrolyl-substituted hydroxamic acid derivatives of the formula

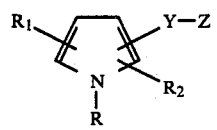
(I)

wherein R represents aryl, aryl-lower alkyl, cycloalkyl, bicycloalkyl or adamantyl; $R_1$ and $R_2$ represent hydrogen or lower alkyl; Y represents a direct bond, lower alkylene, lower alkenylene or lower alkadienylene; Z represents

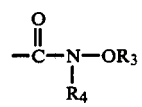
(a)

wherein $R_3$ represents hydrogen or acyl; $R_4$ represents lower alkyl, $C_3$–$C_7$-cycloalkyl, aryl or aryl-lower alkyl; or Z represents

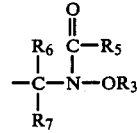
(b)

wherein $R_3$ represents hydrogen or acyl; $R_5$ represents lower alkyl, $C_3$–$C_7$-cycloalkyl, aryl, aryl-lower alkyl, amino or N-(mono- or di-lower alkyl)-amino; $R_6$ and $R_7$ represent hydrogen or lower alkyl; and pharmaceutically acceptable salts thereof provided that $R_3$ represents hydrogen; which are useful as lipoxygenase inhibitors.

18 Claims, No Drawings

CERTAIN PYRROLYL-SUBSTITUTED HYDROXAMIC ACID DERIVATIVES

SUMMARY OF THE INVENTION

The invention relates to the pyrrolyl-substituted hydroxamic acid derivatives as defined herein which are particularly useful as selective lipoxygenase inhibitors, methods for preparation thereof, pharmaceutical compositions comprising said compounds, and a method of inhibiting lipoxygenase and of treating diseases in mammals which are responsive to lipoxygenase inhibition using said compounds or pharmaceutical compositions comprising said compounds of the invention.

The compounds of the invention are particularly useful for the treatment of various inflammatory and allergic conditions, e.g. bronchial allergies and inflammatory disorders such as asthma, ocular allergies and inflammation, and dermatological allergies and inflammation such as psoriasis; also for the treatment of rheumatic disorders such as rheumatoid arthritis.

DETAILED DESCRIPTION OF THE INVENTION

More particularly the invention relates to the compounds of formula I

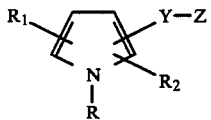

wherein R represents aryl, aryl-lower alkyl, cycloalkyl, bicycloalkyl or adamantyl; $R_1$ and $R_2$ represent hydrogen or lower alkyl; Y represents a direct bond, lower alkylene, lower alkenylene or lower alkadienylene; Z represents

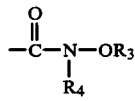

wherein $R_3$ represents hydrogen or acyl; $R_4$ represents lower alkyl, $C_3$–$C_7$-cycloalkyl, aryl or aryl-lower alkyl; or Z represents

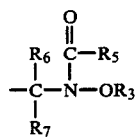

wherein $R_3$ represents hydrogen or acyl; $R_5$ represents lower alkyl, $C_3$–$C_7$-cycloalkyl, aryl, aryl-lower alkyl, amino or N-(mono- or di-lower alkyl)-amino; $R_6$ and $R_7$ represent hydrogen or lower alkyl; and pharmaceutically acceptable salts thereof provided that $R_3$ represents hydrogen.

The grouping Y-Z may be attached at the 2 or 3-position of the pyrrole ring and $R_1$ and $R_2$ are at any of the remaining positions. Preferred are the compounds wherein the group Y-Z is at the 3-position of the pyrrole ring. Also generally preferred are said compounds wherein $R_3$ represents hydrogen, and wherein $R_1$ and $R_2$ are at the 2 and 5 positions of the pyrrole ring.

A particular embodiment of the invention relates to the compounds of formula Ia

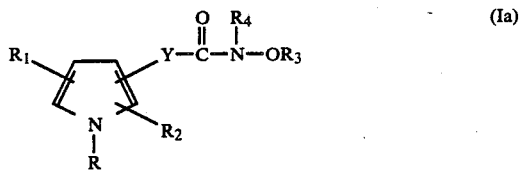

wherein R represents aryl, aryl-lower alkyl, cycloalkyl, bicycloalkyl or adamantyl; $R_1$ and $R_2$ represent hydrogen or lower alkyl; $R_3$ represents hydrogen or acyl; $R_4$ represents lower alkyl, $C_3$–$C_7$-cycloalkyl, aryl or aryl-lower alkyl; Y represents a direct bond, lower alkylene, lower alkenylene or lower alkadienylene; and pharmaceutically acceptable salts of said compounds provided that $R_3$ represents hydrogen.

Preferred are the compounds of formula Ia wherein Y represents lower alkenylene or lower alkylene; R represents aryl, aryl-lower alkyl, cycloalkyl or bicycloalkyl; $R_1$ and $R_2$ represent hydrogen or lower alkyl; $R_3$ represents hydrogen or acyl; $R_4$ represents lower alkyl; and pharmaceutically acceptable salts of said compounds provided that $R_3$ represents hydrogen.

Further preferred are said compounds of formula Ia wherein Y represents lower alkenylene; $R_1$ and $R_2$ represent hydrogen or lower alkyl; $R_3$ represents hydrogen, lower alkanoyl or aroyl; $R_4$ represents lower alkyl; and pharmaceutically acceptable salts thereof provided that $R_3$ represents hydrogen.

Particularly preferred are the said compounds of formula Ia and pharmaceutically acceptable salts thereof wherein the chain bearing the hydroxamic acid group is at the 3-position of the pyrrole ring, and $R_1$ and $R_2$ are at the 2 and 5 positions of the pyrrole ring, which are represented by formula II

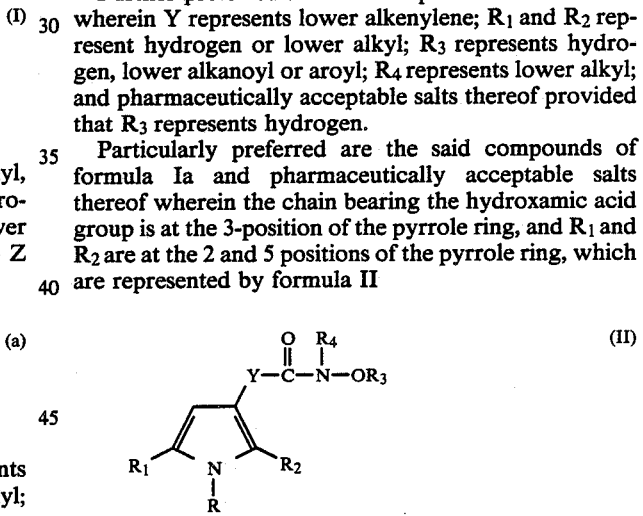

wherein Y, R, and $R_1$–$R_4$ have meanings as defined for compounds of formula Ia.

A particular embodiment thereof relates to compounds of the formula IIa

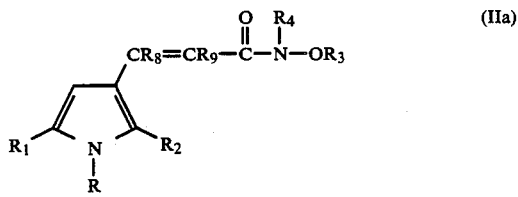

wherein R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represents hydrogen, methyl or ethyl; $R_8$ and $R_9$ independently represent hydrogen, methyl or ethyl; $R_3$ represents hydrogen; $R_4$ represents $C_1$–$C_3$-alkyl; and pharmaceutically acceptable salts thereof.

Further preferred are the compounds of formula IIa and pharmaceutically acceptable salts thereof wherein the pyrrole and hydroxamic acid containing group are trans to each other.

Another embodiment of the invention relates to the compounds of the formula Ib

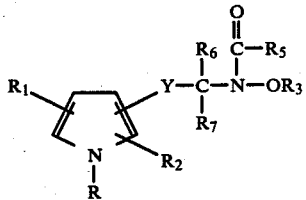

wherein Y represents a direct bond, lower alkylene, lower alkenylene or lower alkadienylene; R represents aryl, aryl-lower alkyl, cycloalkyl, bicycloalkyl or adamantyl; $R_1$ and $R_2$ represent hydrogen or lower alkyl; $R_3$ represents hydrogen or acyl; $R_5$ represents lower alkyl, $C_3$–$C_7$-cycloalkyl, aryl, aryl-lower alkyl, amino or N-(mono- or dialkyl)-amino; $R_6$ and $R_7$ represent hydrogen or lower alkyl; and pharmaceutically acceptable salts thereof provided that $R_3$ represents hydrogen.

Preferred are said compounds of formula Ib wherein Y represents a direct bond or lower alkenylene; R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono- or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represents hydrogen, methyl or ethyl; $R_3$ represents hydrogen, lower alkanoyl or aroyl; $R_5$ represents $C_1$–$C_3$-alkyl, amino or N-(mono- or di-lower alkyl)-amino; $R_6$ represents hydrogen; $R_7$ represents hydrogen or $C_1$–$C_3$ alkyl; and pharmaceutically acceptable salts of said compounds provided that $R_3$ represents hydrogen.

Particularly preferred are the said compounds of formula Ib and pharmaceutically acceptable salts thereof wherein the chain bearing the hydroxamic acid group is at the 3-position of the pyrrole ring and $R_1$ and $R_2$ are at the 2 and 5 positions of the pyrrole rings, which are represented by formula III

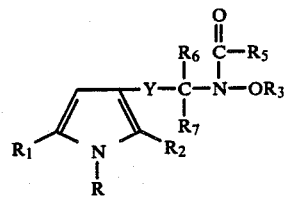

wherein Y, R, $R_1$–$R_3$ and $R_5$–$R_7$ have meanings as defined for compounds of formula Ib.

Preferred are the compounds of formula III wherein Y represents a direct bond and the compounds of formula IIIa

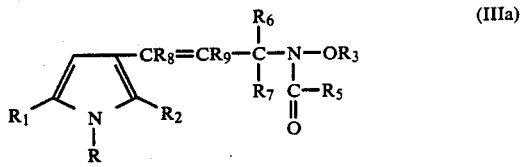

wherein R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represents hydrogen, methyl or ethyl; $R_3$ represents hydrogen; lower alkanoyl or aroyl; $R_5$ represents $C_1$–$C_3$-alkyl, amine or N-(mono or di-lower alkyl)-amino; $R_6$ represents hydrogen; $R_7$, $R_8$ and $R_9$ represent hydrogen or $C_1$–$C_3$-alkyl; and pharmaceutically acceptable salts of said compounds provided that $R_3$ represents hydrogen.

Further preferred are said compounds of formula III and IIIa wherein $R_3$ represents hydrogen, and pharmaceutically acceptable salts thereof.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1–4 carbon atoms, advantageously 1–3 carbon atoms, and represents for example ethyl, propyl, butyl or most advantageously methyl.

A lower alkoxy group preferably contains 1–4 carbon atoms and represents for example ethoxy, propoxy, isopropoxy or advantageously methoxy.

Halogen preferably represents chloro or fluoro but may also be bromo or iodo.

Aryl represents optionally substituted phenyl, e.g. phenyl or phenyl mono-, di- or tri-substituted by one, two or three substituents selected from hydroxy, lower alkyl, halogen, lower alkoxy, trifluoromethyl, cyano, carboxy, lower alkoxycarbonyl, carbamoyl and N-(mono- or dialkyl)-carbamoyl.

Aryl, in aryl or aryl-lower alkyl as specified for substituents $R_4$ and $R_5$, represents preferably phenyl or phenyl mono- or di-substituted by one or two radicals selected from hydroxy, lower alkyl, lower alkoxy and halogen, or mono-substituted by trifluoromethyl or cyano.

Aryl, in aryl or aryl-lower alkyl as specified for substituent R, represents preferably phenyl or phenyl substituted by one, two or three radicals selected from lower alkyl and halogen, or phenyl substituted by a cyano, carbamoyl or N-(mono- or dialkyl)-carbamoyl group.

Aryl-lower alkyl represents for example benzyl or phenylethyl.

Acyl is preferably lower alkanoyl or aroyl.

Lower alkanoyl represents preferably $C_2$–$C_4$-alkanoyl such as acetyl or propionyl.

Aroyl represents preferably benzoyl or benzoyl mono- or di-substituted by one or two radicals selected from lower alkyl, lower alkoxy and halogen; or benzoyl monosubstituted by cyano or trifluoromethyl; or 1- or 2-naphthoyl.

Cycloalkyl represents $C_3$-$C_7$-cycloalkyl, preferably $C_5$-$C_7$-cycloalkyl.

$C_3$-$C_7$-cycloalkyl represents cyclopropyl, cyclobutyl, cyclopentyl, cyclohexyl or cycloheptyl.

Bicycloalkyl represents preferably bicycloheptyl or bicycloheptyl substituted by lower alkyl, particularly unsubstituted or lower alkyl substituted bicyclo[2,2,1]heptyl, such as bornyl, isobornyl, norbornyl, e.g. 2-norbornyl. The term "bornyl" is synonymous with "bornanyl".

Adamantyl represents preferably 1-adamantyl.

Lower alkylene represents either straight chain or branched $C_1$-$C_7$-alkylene, and represents preferably a methylene, ethylene, propylene or butylene chain, or said methylene, ethylene, propylene or butylene chain monosubstituted by $C_1$-$C_3$-alkyl or disubstituted on the same or different carbon atoms by $C_1$-$C_3$ alkyl (advantageously methyl), the total number of carbon atoms being up to and including 7.

Lower alkenylene represents $C_2$-$C_7$-alkenylene, may be straight chain or branched and represents preferably straight chain $C_2$-$C_4$-alkenylene or said straight chain $C_2$-$C_4$-alkenylene substituted on either saturated or unsaturated carbon atoms in the chain by one or two of $C_1$-$C_3$-alkyl, advantageously methyl, the total number of carbon atoms being up to and including 7.

Lower alkadienylene represents $C_4$-$C_7$-alkadienylene and represents preferably 1,3-butadienylene ($C_4$-alkadienylene), unsubstituted or substituted by $C_1$-$C_3$-alkyl (advantageously methyl), the total number of carbon atoms being up to and including 7.

Pharmaceutically acceptable salts of the acidic compounds of the invention (provided that $R_3$ represents hydroxy) are salts formed with bases, namely cationic salts such as alkali and alkaline earth metal salts, such as sodium, lithium, potassium, calcium, magnesium, as well as ammonium salts, such as ammonium, trimethylammonium, diethylammonium, tris-(hydroxymethyl)-methylammonium salts.

The compounds of the invention exhibit valuable pharmacological properties in mammals, and are particularly useful as selective 5-lipoxygenase inhibitors for the treatment of e.g. inflammatory and allergic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-8}$ molar concentrations. The dosage in vivo may range, depending on the route of administration, between about 0.01 and 30 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocyte-chemoattractant, smooth muscle-constricting and vascular permeability-enhancing properties. $LTB_4$ is among the most potent leukocyte chemotactic agents known $LTC_4$, $LTD_4$ and $LTE_4$ are the components of the "slow-reacting substance of anaphylaxis" (SRS-A) and are potent inducers of broncho-constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, selective inhibition of 5-lipoxygenase will suppress biosynthesis of leukotrienes in leukocytes and various organ systems.

5-Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (Nature 287: 51, 1980) used to measure the formation of 5-HETE and $LTB_4$-like products from $^{14}C$-arachidonic acid. $IC_{50}$ values are determined graphically as the concentration of test compound at which the synthesis of 5-HETE and $LTB_4$-like products is reduced to 50% of their respective control values.

The inhibition of $LTB_4$ formation can also be determined in vitro in whole blood from dogs. One ml samples of blood are preincubated at 37° C. for 5 minutes with the desired concentration of test compound added as a solution in 10 microliters of dimethylsulfoxide. $LTB_4$ synthesis is then stimulated by the addition of A-23187 and N-formyl-met-leu-phe (f-MLP). The amount of $LTB_4$ is measured in the separated plasma fraction by radioimmunoassay. $IC_{50}$ values are determined graphically as the concentration of test compound causing 50% inhibition of $LTB_4$ formation seen in control whole blood.

Furthermore, the inhibition of 5-lipoxygenase is determined after oral or i.v. administration to rats or dogs by measuring ex vivo in whole blood the decrease of A-23187-stimulated $LTB_4$ formation as compared to non-treated control animals.

Antiinflammatory activity is demonstrated by measuring the inhibition of the edema and inhibition of the influx of polymorphonuclear (PMN's) and mononuclear leucocytes (monocytes) after oral administration in the rat model in which pleurisy is first induced by injecting carrageenin into the pleural cavity, e.g. according to A. P. Almeida et al, J. Pharmacol. Exp. Therap. 214, 74 (1980).

Illustrative of the invention, the compound of example 1a, (E)-3-(1-cycloheptyl-1H-pyrrol-3-yl)-N-hydroxy-N-methyl-2-propenamide, inhibits the formation of 5-HETE [(5S)-5-hydroxy-6,8,11,14-eicosatetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, e.g. at an $IC_{50}$ of about 0.1 micromolar ($1 \times 10^{-7}M$). Said compound also inhibits by 50% $LTB_4$ formation as determined ex vivo when administered at a dose of about 3 mg/kg p.o. to the dog.

Furthermore, the compound of example 1a, at 10 mg/kg p.o. administered for two days at −1, 6, 24 and 45 hours relative to the carrageenin injection, causes inhibition of exudate volume 48 hours after injection of carrageenin in the rat pleurisy model of inflammation.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders (such as asthma), dermatological allergies and inflammatory disorders (such as psoriasis), also arthritic inflammatory disorders (such as rheumatoid arthritis), as well as ocular allergies and inflammatory disorders.

The compounds of the invention, depending on the structural type involved, can be prepared by the following synthetic processes:

(1) for compounds of formula Ia
(a) condensing a compound of formula IV

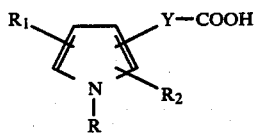

or a reactive functional derivative thereof, wherein R, $R_1$, $R_2$ and Y have meaning as defined hereinabove, with a compound of the formula V $$R_4-NH-OR_3 \quad (V)$$

wherein $R_3$ and $R_4$ have meaning as defined herein, optionally in protected form when $R_3$ represents hydrogen; and (2) for compounds of formula Ib
(b) condensing a compound of the formula VI

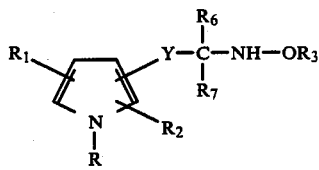

wherein Y, R, $R_1$, $R_2$, $R_3$, $R_6$ and $R_7$ have meaning as defined hereinabove with a compound of the formula VII $$R_5-COOH \quad (VII)$$

or a reactive functional derivative thereof, wherein $R_5$ represents lower alkyl, $C_3$-$C_7$-cycloalkyl, aryl, aryl-lower alkyl or di-lower alkylamino; or (c) condensing a compound of the formula VI above with phosgene followed by ammonia, a mono lower alkylamine or a di-lower alkylamine; or (d) condensing a compound of the formula VI above with a lower alkyl isocyanate.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into a free compound or into another salt; and/or a mixture of isomers or racemates obtained is separated into the single isomers or racemates; and/or, if desired, a racemate is resolved into the optical antipodes.

In starting compounds and intermediates which are converted to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

Also, a reactive esterified derivative of an alcohol in any of the processes cited herein represents said alcohol esterified by a strong acid, especially a strong inorganic acid, such as a hydrohalic acid, especially hydrochloric, hydroboromic or hydriodic acid, or sulphuric acid, or by a strong organic acid, especially a strong organic sulfonic acid, such as an aliphatic or aromatic sulfonic acid, for example methanesulfonic aid, 4-methylphenylsulfonic acid or 4-bromophenylsulfonic acid. A said reactive esterified derivative is especially halo, for example chloro, bromo or iodo, or aliphatically or aromatically substituted sulfonyloxy, for example methylsulfonyloxy or 4-methylphenylsulfonyloxy (tosyloxy).

The above processes for the synthesis of compounds of the invention can be carried out according to methodology generally known in the art for the preparation of hydroxamic acids and derivatives thereof.

The synthesis according to process (a) involving the condensation of a free carboxylic acid of formula IV with an optionally hydroxy protected hydroxylamine derivative of formula V can be carried out in the presence of a condensing agent, e.g. diethyl phosphorocyanidate, 1,1'-carbonyldiimidazole or dicyclohexylcarbodiimide, in an inert polar solvent, such as dimethylformamide or methylene chloride.

The synthesis according to process (a) involving the condensation of a reactive functional derivative of an acid of formula IV as defined above, e.g. an acid chloride or mixed anhydride with an optionally hydroxy protected hydroxylamine derivative of formula V, or a salt thereof in presence of a base such as triethylamine can be carried out, at a temperature ranging preferably from about −78° to +75°, in an inert organic solvent such as dichloromethane or toluene.

The synthesis according to process (b) involving the condensation of a carboxylic acid of formula VII or a reactive functional derivative thereof with a hydroxylamine derivative of formula VI (optionally hydroxy protected when $R_3$ represents hydrogen) is essentially carried out as generally described for process (a).

In the case of acylation of the compounds of formula VI wherein $R_3$ represents hydrogen, e.g. with 2 mole equivalents or excess of a functional derivative of a compound of formula VII, the N,O-bis-acylated compounds of formula Ib, namely those wherein $R_3$ represents $COR_5$, are obtained. The N,O-diacylated compounds of formula Ib, e.g. wherein $R_5$ represents lower alkyl and $R_3$ represents the corresponding $COR_5$ group, can be selectively O-deacylated under basic conditions, e.g. with potassium carbonate in a hydroxylic solvent such as methanol to yield the corresponding compounds of formula Ib wherein $R_3$ represents hydrogen.

Processes (c) and (d) are directed to the preparation of urea derivatives, the compounds of formula I wherein Z represents group (b), i.e. of formula Ib wherein $R_5$ represents amino or substituted amino, from hydroxylamines of formula VI.

The preparation according to process (c) can be carried out by reacting the hydroxylamine derivative of formula VI, preferably in hydroxy-protected form, with phosgene in an inert solvent such as toluene in the presence of e.g. triethylamine, followed by condensation with the appropriate amine at a temperature of about −25° C. to +50° C.

The preparation according to process (d) involves the condensation of a hydroxylamine of formula VI, preferably in hydroxy-protected form, with a lower alkyl isocyanate in an inert solvent such as toluene at a temperature ranging from room temperature to reflux temperature.

Protected forms of hydroxylamines of formula V and VI (wherein $R_3$ represents hydrogen) in the above processes are those wherein the hydroxy group is protected for example as a benzyl ether or tetrahydropyranyl ether. Removal of said protecting groups is carried out according to methods well known in the art, e.g. hydrogenolysis or acid hydrolysis, respectively.

The starting materials of formula IV can be prepared according to methods generally known in the art for converting the aldehyde function of a compound of the formula VIII

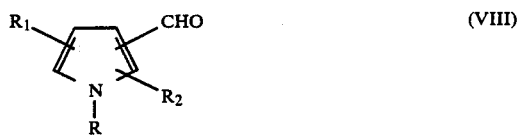 (VIII)

wherein R, $R_1$ and $R_2$ have meaning as previously defined to functional grouping Y—COOH in a corresponding compound of the formula IV, e.g. as illustrated herein.

The compounds of formula VIII can in turn be prepared from the corresponding pyrrole of the formula IX

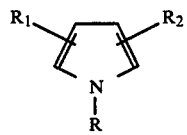 (IX)

wherein R, $R_1$ and $R_2$ have meaning as defined hereinabove by treatment with dimethylformamide in the presence of e.g. phosphorous oxychloride.

The formyl group is introduced at either the 2- or 3-position of the pyrrole ring depending on nature of the substituents. For example, if $R_1$ and $R_2$ represent lower alkyl at the 2- and 5-positions then the formyl group is introduced at the 3-position; if $R_1$ and $R_2$ represent hydrogen then the formyl group is introduced at the 2-and/or 3-position.

The intermediates of formula IX are in turn prepared according to methods known in the art, e.g. by condensing a compound of the formula X

R—NH$_2$ (X)

wherein R has meaning as previously defined with e.g. 2,5-dimethoxytetrahydrofuran or a compound of the formula

$R_1$—COCH$_2$CH$_2$CO—$R_2$ (XI)

wherein $R_1$ and $R_2$ have meaning as previously defined.

Intermediates of formula VIII, those wherein the formyl grouping is at the 3-position of the pyrrole ring may also be prepared by condensing a compound of the formula X with e.g. a compound of the formula XII

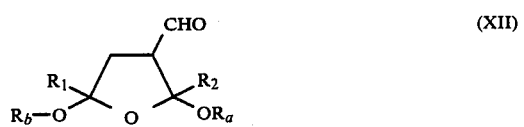 (XII)

wherein $R_1$ and $R_2$ have meaning as previously defined, and $R_a$ and $R_b$ represent lower alkyl, in an inert solvent such as toluene, optionally in the presence of an anhydrous acid so as to obtain compounds of formula VIII wherein $R_1$ and $R_2$ are at the 2- and 5-positions and the formyl group is at the 3-position.

The acids of formula VII, diketones or dialdehydes of formula XI and tetrahydrofuran derivatives of formula XII are either known in the art or can be prepared according to methods known in the art.

The hydroxylamine derivatives of formula V are known or are prepared according to methods well-known in the art for the preparation of hydroxylamines e.g. by condensing corresponding halides with e.g. benzyl or tetrahydropyranyl O-protected hydroxylamine, by reduction of oximes or reduction of nitro compounds (particularly if $R_4$ represents aryl).

The starting hydroxylamines of formula VI in protected form may be prepared from a corresponding reactive derivative of an alcohol of formula XIII

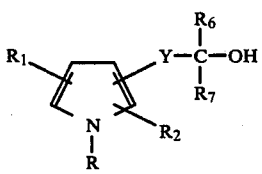

(XIII)

wherein R, R$_1$, R$_2$, Y, R$_6$ and R$_7$ have meaning as defined herein, such as the corresponding bromide, tosylate or mesylate derivative, by condensing such with e.g. O-benzylhydroxylamine or O-tetrahydropyranylhydroxylamine.

Alternately hydroxylamines of formula VI wherein at least one of R$_6$ and R$_7$ represents hydrogen can be prepared from the corresponding aldehyde or ketone by conversion to the oxime with e.g. hydroxylamine hydrochloride according to known methods, followed by reduction to the hydroxylamine with e.g. diborane or sodium cyanoborohydride in acidic medium.

The alcohols of formula XIII or corresponding aldehydes or ketones may be prepared e.g. from the corresponding acids of formula IV or ester derivatives thereof according to methods well-known in the art. For example, such can be reduced to the alcohol wherein R$_6$ and/or R$_7$ represent hydrogen using an appropriate reducing agent such as lithium aluminum hydride, aluminum hydride and the like. For compounds wherein Y represents a direct bond, the aldehyde starting materials represent the above-cited aldehydes of formula VIII. The corresponding ketones can be prepared by treatment of a pyrrole of formula IX with a reactive functional derivative of e.g. a lower alkanoic acid, such as acetyl chloride in the presence of a Lewis acid catalyst.

The carboxylic acids of formula VII and reactive derivatives thereof are known in the art or can be prepared according to methods well-known in the art.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

Compounds of the invention can also be converted into each other according to methods generally known per se, e.g. by hydrogenation of one or more double bonds in linking group Y.

The invention also relates to any novel starting materials and processes for their manufacture.

Depending on the choice of starting materials and methods, the new compounds may be in the form of one of the possible isomers or mixtures thereof, for example, as substantially pure geometric (Z or E, cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, in known manner, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids (wherein R$_3$ represents hydrogen) can thus be resolved into their optical antipodes e.g. by fractional crystallization of d- or l-(alpha-methylbenzylamine, cinchonidine, cinchonine, quinine, quinidine, ephedrine, dehydroabiethylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit 5-lipoxygenase and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention also relates to a method of inhibiting 5-lipoxygenase activity in mammals and treating diseases and conditions responsive thereto, particularly inflammatory and allergic disorders, which comprises administering to a mammal in need thereof an effective amount of a compound of the invention or of a pharmaceutical composition comprising a said compound in combination with one or more pharmaceutically acceptable carriers.

The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR).

EXAMPLE 1

(a) A solution of 7.0 g of (E)-3-(1-cycloheptyl-1H-pyrrol-3-yl)-2-propenoic acid and 2.3 g dimethylformamide in 200 ml of dichloromethane is cooled in an ice bath and 6.2 ml oxalyl chloride is added dropwise. The solution is stirred in an ice bath for 90 minutes. This solution is added all at once to a solution of 10 g N-methyl hydroxylamine hydrochloride in 25 ml water, 25 ml triethylamine and 100 ml tetrahydrofuran. The reaction mixture is stirred in an ice bath for 2 hours, then washed with cold dilute hydrochloric acid. The organic phase is separated, dried over magnesium sulfate, treated with charcoal and evaporated to dryness at 50° under reduced pressure. The residue is crystallized from ether to yield (E)-3-(1-clopheptyl-1H-pyrrol-3-yl)-N-hydroxy-N-methyl-2-propenamide, m.p. 98°–100°, which can also be named (E)-3-(1-cycloheptyl-1H-pyrrol-3-yl)-N-hydroxy-N-methyl-2-propenohydroxamic acid.

A solution of 1 mole equivalent of sodium hydroxide in methanol is added to a solution of the above hydroxamic acid in dichloromethane and the resulting solution is evaporated to dryness to yield the sodium salt, namely sodium (E)-3-(1-cycloheptyl-1H-pyrrol-3-yl)-N-methyl-N-hydroxy-2-propenohydroxamate, m.p. 202°–204°.

The starting material is prepared as follows:

A mixture of 38.0 g of cycloheptylamine and 50 ml of 2,5-dimethoxytetrahydrofuran-3-carboxaldehyde in 300 ml of glacial acetic acid is stirred under reflux for 3 hours. The solution is evaporated to dryness at 60° under reduced pressure. The residue is then dissolved in a 1:1 mixture of ether and hexane, the solution is treated with charcoal and evaporated to dryness to give 1-cycloheptyl-1H-pyrrole-3-carboxaldehyde as an oil. The aldehyde (30 g) is then added dropwise to a mixture of 35 ml of triethyl phosphonoacetate in 1 liter of toluene to which had been added 9.5 g of sodium hydride. The reaction mixture is stirred in an ice bath for 2 hours and then at room temperature overnight, washed first with ice cold dilute hydrochloric acid, then with brine, dried over magnesium sulfate, treated with charcoal and evaporated to dryness to yield ethyl (E)-3-(1-cycloheptyl-1H-pyrrol-3-yl)-2-propenoate.

A solution of 38 g of the ester in 400 ml ethanol and 200 ml of 1.5N aqueous sodium hydroxide is stirred at room temperature for 16 hours. The ethanol is evaporated at 50° and reduced pressure and the basic solution is washed with ethyl acetate, made acidic with ice cold 5N aqueous hydrochloric acid and extracted into ethyl acetate; the extract is washed with brine, dried over MgSO$_4$, treated with charcoal and filtered. The solvent is evaporated at 50° and reduced pressure and the residue is crystallized from ether to yield (E)-3-(1-cycloheptyl-1H-pyrrol-3-yl)-2-propenoic acid, m.p. 138°–140°.

Similarly prepared are the following:

(b) (E)-3-[1-(2,4,6-trimethylbenzyl)-1H-pyrrol-3-yl]-N-hydroxy-N-methyl-2-propenamide, m.p. 162°–164°; corresponding carboxylic acid, m.p. 168°–170°.

(c) (E)-3-[1-(2,6-dimethylphenyl)-1H-pyrrol-3-yl]-N-hydroxy-N-methyl-2-propenamide, m.p. 156°–158°; corresponding carboxylic acid, m.p. 160°–162°.

(d) (E)-3-[1-(2-norbornanyl)-1H-pyrrol-3-yl]-N-hydroxy-N-methyl-2-propenamide, m.p. 95°–97°.

(e) (E)-3-[1-(2,6-dichlorophenyl)-1H-pyrrol-3-yl]-N-hydroxy-N-methyl-2-propenamide, m.p. 174°–176°; corresponding carboxylic acid, m.p. 188°–190°.

(f) (E)-3-[1-(2,4,6-trimethylphenyl)-1H-pyrrol-3-yl]-N-hydroxy-N-methyl-2-propenamide, m.p. 162°–164°; corresponding carboxylic acid, m.p. 118°–120°.

(g) (E)-3-[1-(2,6-dichloro-3-methylphenyl)-1H-pyrrol-3-yl]-N-hydroxy-N-methyl-2-propenamide, m.p. 151°–153°; corresponding carboxylic acid, m.p. 176°–178°.

(h) (E)-3-[1-(2-methylphenyl)-1H-pyrrol-3-yl]-N-hydroxy-N-methyl-2-propenamide, m.p. 115°–117°; corresponding carboxylic acid, m.p. 193°–195°.

(i) (E)-3-[1-(2,6-dimethylphenyl)-1H-pyrrol-3-yl]-N-hydroxy-N,2-dimethyl-2-propenamide, m.p.

111°–113°; corresponding carboxylic acid, m.p. 166°–168° which is prepared as illustrated in procedure under (a), replacing triethyl phosphonoacetate with triethyl 2-phosphonopropionate.

(j) (E)-5-[1-(2,6-dimethylphenyl)-1H-pyrrol-3-yl]-N-hydroxy-N-methyl-2,4-pentadienamide, m.p. 138°–140°; corresponding carboxylic acid, m.p. 168°–170° which is prepared as illustrated in procedure under (a) replacing triethylphosphonoacetate with triethyl phosphonocrotonate.

(k) (E)-3-[1-(alpha-methylbenzyl)-2,5-dimethyl-1H-pyrrol-3-yl]-N-hydroxy-N-methyl-2-propenamide, m.p. 35°–37°; corresponding carboxylic acid, m.p. 62°–65°.

(l) (E)-3-[1-(2,6-diisopropylphenyl)-1H-pyrrol-3-yl]-N-hydroxy-N-methyl-2-propenamide, m.p. 181°–183°; corresponding carboxylic acid, m.p. 180°–182°.

(m) (E)-3-[1-(2,6-diethylphenyl)-1H-pyrrol-3-yl]-N-hydroxy-N-methyl-2-propenamide, m.p. 154°–156°; corresponding carboxylic acid, m.p. 85°–87°.

(n) (E)-3-[1-(2-fluoro-4,6-dimethylphenyl)-1H-pyrrol-3-yl]-N-hydroxy-N-methyl-2-propenamide, m.p. 158°–160°; corresponding carboxylic acid, m.p. 157°–159°.

(o) (E)-3-[1-(4-fluoro-2,6-dimethylphenyl)-1H-pyrrol-3-yl]-N-hydroxy-N-methyl-2-propenamide, m.p. 167°–169°; corresponding carboxylic acid, m.p. 202°–204°.

(p) (E)-3-[1-(2,4,6-trifluorophenyl)-1H-pyrrol-3-yl]-N-hydroxy-N-methyl-2-propenamide, m.p. 155°–157°; corresponding carboxylic acid, m.p. 228°–230°.

(q) (E)-3-[1-(2,6-dibromo-4-methylphenyl)-1H-pyrrol-3-yl]-N-hydroxy-N-methyl-2-propenamide, m.p. 185°–187°; corresponding carboxylic acid, m.p. 178°–180°.

(r) (E)-3-[1-(1-adamantyl)-1H-pyrrol-3-yl]-N-hydroxy-N-methyl-2-propenamide.

(s) (E)-3-(1-cyclohexyl-1H-pyrrol-3-yl)-N-hydroxy-N-methyl-2-propenamide.

EXAMPLE 2

(a) (E)-3-[1-(4-Dimethylcarbamoylphenyl)-2,5-dimethyl-1H-pyrrol-3-yl]-2-propenoic acid is condensed with N-methylhydroxylamine as described in example 1(a) to yield (E)-3-[1-(4-dimethylcarbamoylphenyl)-2,5-dimethyl-1H-pyrrol-3-yl]-N-hydroxy-N-methyl-2-propenamide, m.p. 172°–174°.

The starting material is prepared as follows:

A solution of 26.4 g of 4-amino-N,N-dimethylbenzamide in 500 ml toluene and 60 g acetonylacetone is refluxed for 16 hours under a Dean-Stark water separator. The solution is washed with water and brine, dried over MgSO4, filtered and the solvent evaporated at 60° and reduced pressure. The residue is crystallized from ether-hexane 1:1 to yield 1-(4-dimethylcarbamoylphenyl)-2,5-dimethyl-1H-pyrrole, m.p. 102°–104°.

A mixture of 25 g of this pyrrole in 300 ml ether, 25 ml dimethylformamide and 25 ml phosphorous oxychloride is refluxed with stirring for 7 hours. The reaction is cooled, the ether is decanted and discarded, the residue is treated with crushed ice, basified with 6N aqueous sodium hydroxide and extracted into ethyl acetate. The extract is dried over MgSO4, treated with charcoal and filtered. The solvent is evaporated at 50° and reduced pressure to give 1-(4-dimethylcarbamoylphenyl)-2,5-dimethyl-1H-pyrrole-3-carboxyaldehyde as an oil.

The aldehyde is then reacted with sodium hydride and triethyl phosphonoacetate according to the procedure previously described in example 1(a), and the resulting ester is hydrolyzed to yield (E)-3-[1-(4-dimethylcarbamoylphenyl)-2,5-dimethyl-1H-pyrrol-3-yl]-2-propenoic acid, m.p. 182°–184°.

(b) Similarly prepared is (E)-3-[1-(4-fluorophenyl)-2,5-dimethyl-1H-pyrrol-3-yl]-N-hydroxy-N-methyl-2-propenamide, m.p. 170°–172°; corresponding carboxylic acid, m.p. 208°–210°.

EXAMPLE 3

Condensation of (Z)-3-[1-(2,6-dimethylphenyl)-1H-pyrrol-3-yl]-2-butenoic acid is condensed with N-methylhydroxylamine as described in example 1(a) to yield (Z)-3-[1-(2,6-dimethylphenyl)-1H-pyrrol-3-yl]-N-hydroxy-N-methyl-2-butenamide, m.p. 158°–160°.

The starting material is prepared as follows:

A solution of 2,6-dimethylaniline (60.5 g), glacial acetic acid (600 ml) and 2,5-dimethoxytetrahydrofuran (572 g) is refluxed for 5 hours. The solvent is evaporated at 60° and reduced pressure to give 1-(2,6-dimethylphenyl)-1H-pyrrole as an oil.

Then, a solution of 8.5 g of this pyrrole in 150 ml toluene and 3.5 ml acetyl chloride is stirred at 0° and 6 ml stannic chloride is added dropwise. After addition the mixture is stirred for 2 hours at room temperature, 100 ml ice cold aqueous 5N hydrochloric acid is added and the mixture is kept for 1 hour. The organic phase is separated, washed with brine, dried over MgSO4, treated with charcoal and filtered. The solvent is evaporated at 50° and reduced pressure to give 1-(2,6-dimethylphenyl)-3-acetyl-1H-pyrrole as an oil.

Condensation with sodium hydride and triethyl phosphonoacetate according to procedure in example 1(a) yields (Z)-3-[1-(2,6-dimethylphenyl)-1H-pyrrol-3-yl]-2-butenoic acid, m.p. 78°–80°.

EXAMPLE 4

(a) Acetyl chloride (1 ml) is added while stirring to a solution of 1.0 g of N-hydroxy-1-[1-(2,6-dimethylphenyl)-1H-pyrrol-3-yl]-ethylamine and 2 ml of triethylamine in 100 ml of methylene chloride at 0°. The reaction mixture is stirred for 2 hours, washed with ice cold dilute hydrochloric acid, water, dried over magnesium sulfate, treated with charcoal, filtered and evaporated to dryness to yield N-acetyl-N-acetyloxy-1-[1-(2,6-dimethylphenyl)-1H-pyrrol-3-yl]-ethylamine as an oil.

The starting material is prepared as follows:

A mixture of 1-(2,6-dimethylphenyl)-3-acetyl-1H-pyrrole (20.0 g), hydroxylamine hydrochloride (25.0 g), pyridine (130 ml) in 100 ml of methanol is heated under reflux for 20 hours. Workup in the usual manner yields 1-(2,6-dimethylphenyl)-3-acetyl-1H-pyrrole oxime.

Two mole-equivalents of sodium cyanoborohydride is added to a mixture of 1-(2,6-dimethylphenyl-3-acetyl-1H-pyrrole oxime in methanol and ethanolic hydrochloric acid is added to adjust to pH 3. The reaction mixture is stirred at room temperature overnight, poured over ice, rendered basic and extracted with ether. The ether extract is washed with brine, dried and evaporated to dryness. The residue is chromatographed over silica gel by gradient elution with methylene chloride/methanol, to yield N-hydroxy-1-[1-(2,6-dimethylphenyl)-1H-pyrrol-3-yl]-ethylamine.

(b) Similarly prepared is N-acetyl-N-acetyloxy-1-(1-cycloheptyl-1H-pyrrol-3-yl)-ethylamine.

(c) Similarly prepared is N-acetyl-N-acetyloxy-3-[1-(2,6-dimethylphenyl)-1H-pyrrol-3-yl]-allylamine. The starting material is prepared by condensing 1-(2,6-dimethylphenyl)-1H-pyrrole-3-carboxaldehyde with diethyl phosphonoacetaldehyde diethylacetal to obtain 3-[1-(2,6-dimethylphenyl)-1H-pyrrol-3-yl]-acrolein. The aldehyde is then converted to the oxime and reduced to the hydroxylamine according to previously described procedures.

EXAMPLE 5

(a) A mixture of 1.0 g of N-acetyl-N-acetyloxy-1-[1-(2,6-dimethylphenyl-1H-pyrrol-3-yl]-ethylamine and 5.0 g of potassium carbonate in 50 ml of methanol is stirred at room temperature overnight and then evaporated to dryness. The residue is suspended in water and the product is extracted with ethyl acetate. The ethyl acetate extract is washed with brine, dried and evaporated to dryness. The residue is purified by chromatography on silica gel to yield N-acetyl-N-hydroxy-1-[1-(2,6-dimethylphenyl)-1H-pyrrol-3-yl]-ethylamine.

(b) Similarly prepared is N-acetyl-N-hydroxy-1-[1-cycloheptyl-1H-pyrrol-3-yl]-ethylamine.

(c) Similarly prepared is N-acetyl-N-hydroxy-3-[1-(2,6-dimethylphenyl)-1H-pyrrol-3-yl]-allylamine.

EXAMPLE 6

(a) A solution of 1.0 g of N-hydroxy-1-[1-(2,6-dimethylphenyl)-1H-pyrrol-3-yl]-ethylamine in 60 ml of toluene is stirred and treated first with one mole equivalent of 4.0M ethanolic HCl, followed by 10 ml of 2.0M phosgene in toluene. The solution is stirred for 7 hours, 50 ml of concentrated ammonium hydroxide is added and the mixture is stirred overnight. Excess water is then added and the mixture is again stirred for 2 hours. The organic layer is separated, washed with brine, dried over magnesium sulfate, treated with charcoal and evaporated to dryness to yield N-carbamoyl-N-hydroxy-1-[1-(2,6-dimethylphenyl)-1H-pyrrol-3-yl]-ethylamine.

(b) Similarly prepared is N-carbamoyl-N-hydroxy-3-[1-(2,6-dimethylphenyl)-1H-pyrrol-3-yl]-allylamine.

EXAMPLE 7

A solution of 1.0 g of N-(N'-methylcarbamoyl)-N-benzyloxy-1-[1-(2,6-dimethylphenyl)-1H-pyrrol-3-yl]-ethylamine in 50 ml of ethyl acetate is hydrogenated at room temperature and 3 atmospheres pressure for 3 hours to yield N-(N'-methylcarbamoyl)-N-hydroxy-1-[1-(2,6-dimethylphenyl)-1H-pyrrol-3-yl]-ethylamine.

The starting material is prepared as follows:

O-Benzylhydroxylamine hydrochloride (8.0 g) is added to a solution of 9.0 g of 1-(2,6-dimethylphenyl)-3-acetyl-1H-pyrrole in 200 ml of methanol, and the mixture is stirred for 3 hours. The solvent is removed under reduced pressure, the residue is dissolved in 300 ml of hexane and the solution is washed first with 2N aqueous hydrochloric acid and then brine. The organic layer is dried over magnesium sulfate, treated with charcoal and evaporated to dryness to yield O-benzyl 1-(2,6-dimethylphenyl)-3-acetyl-1H-pyrrole oxime.

A solution of 6.5 g of O-benzyl 1-(2,6-dimethylphenyl)-3-acetyl-1H-pyrrole oxime in 150 ml ethyl acetate is treated with 8 g of borane-pyridine complex followed by 45 ml of 6N aqueous hydrochloric acid. The mixture is stirred for 16 hours, poured over ice, made alkaline to pH 9 and extracted with ether. The ether extract is washed with brine, dried over magnesium sulfate and filtered to yield N-benzyloxy-1-[1-(2,6-dimethylphenyl)-1H-pyrrol-3-yl]-ethylamine.

Methyl isocyanate (5 ml) is added to a solution of 2.1 g of N-benzyloxy-1-[1-(2,6-dimethylphenyl)-1H-pyrrol-3-yl]-ethylamine in 200 ml of ether and the solution is stirred at room temperature for 24 hours. Excess water is added and the mixture is stirred for 3 hours. The organic layer is separated, washed with brine, dried over magnesium sulfate and evaporated to dryness to yield N-(N'-methylcarbamoyl)-N-benzyloxy-1-[1-(2,6-dimethylphenyl)-1H-pyrrol-3-yl]-ethylamine.

EXAMPLE 8

(a) Preparation of 10,000 tablets each containing 20 mg of the active ingredient, having the formula as follows:

| | |
|---|---|
| (E)-3-(1-cycloheptyl-1H-pyrrol-3-yl)-N-hydroxy-N-methyl-2-propenamide | 200.00 g |
| Lactose | 2,535.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10-100 mg of one of the other compounds disclosed and exemplified herein.

(b) Preparation of 1,000 capsules each containing 10 mg of the active ingredient, having the formula as follows:

| | |
|---|---|
| (E)-3-(1-cycloheptyl-1H-pyrrol-3-yl)-N-hydroxy-N-methyl-2-propenamide | 10.00 g |
| Lactose | 207.00 g |
| Modified starch | 80.00 g |
| Magnesium stearate | 3.00 g |

Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing about 10-100 mg of the other compounds disclosed and exemplified herein.

What is claimed is:

1. A compound of the formula

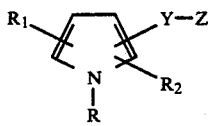

wherein R represents aryl, aryl-lower alkyl, cycloalkyl, bicycloalkyl or adamantyl; $R_1$ and $R_2$ represent hydrogen or lower alkyl; Y represents a direct bond, lower alkylene, lower alkenylene or lower alkadienylene; Z represents

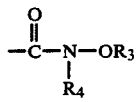

(a)

wherein $R_3$ represents hydrogen ore acyl; $R_4$ represents lower alkyl, $C_3$–$C_7$-cycloalkyl, aryl or aryl-lower alkyl; or Z represents

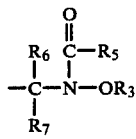

(b)

wherein $R_3$ represents hydrogen or acyl; $R_5$ represents lower alkyl, $C_3$–$C_7$-cycloalkyl, aryl, aryl-lower alkyl, amino or N-(mono- or di-lower alkyl)-amino; $R_6$ and $R_7$ represent hydrogen or lower alkyl; aryl in the above definitions represents phenyl or phenyl mono-, di- or tri-substituted by one, two or three substituents selected from hydroxy, lower alkyl, halogen, lower alkoxy, trifluoromethyl, cyano, carboxy, lower alkoxycarbonyl, carbomyl and N-(mono- or dialkyl)-carbamoyl; acyl represents lower alkanoyl or aroyl; and aroyl represents benzoyl or benzoyl mono- or di-substituted by one or two radicals selected from lower alkyl, lower alkoxy and halogen, or benzoyl monosubstituted by cyano or trifluoromethyl, or 1- or 2-naphthoyl; or a pharmaceutically acceptable salt thereof provided that $R_3$ represents hydrogen.

2. A compound according to claim 1 of the formula

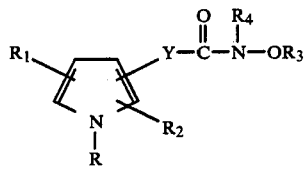

(Ia)

wherein R represents aryl, aryl-lower alkyl, cycloalkyl, bicycloalkyl or adamantyl; $R_1$ and $R_2$ represent hydrogen or lower alkyl; $R_3$ represents hydrogen or acyl; $R_4$ represents lower alkyl, $C_3$–$C_7$-cycloalkyl, aryl or aryl-lower alkyl; Y represents a direct bond, lower alkylene, lower alkenylene or lower alkadienylene; or a pharmaceutically acceptable salt thereof provided that $R_3$ represents hydrogen.

3. A compound according to claim 2 of formula Ia wherein Y represents lower alkenylene or lower alkylene; R represents aryl, aryl-lower alkyl, cycloalkyl or bicycloalkyl; $R_1$ and $R_2$ represent hydrogen or lower alkyl; $R_3$ represents hydrogen or acyl; $R_4$ represents lower alkyl; or a pharmaceutically acceptable salt thereof provided that $R_3$ represents hydrogen.

4. A compound according to claim 2 wherein Y represents lower alkenylene; or a pharmaceutically acceptable salt thereof provided that $R_3$ represents hydrogen.

5. A compound according to claim 2 of the formula

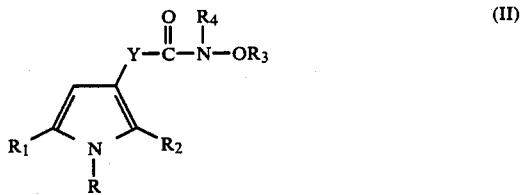

(II)

wherein Y represents lower alkenylene or lower alkylene; R represents aryl, aryl-lower alkyl, cycloalkyl or bicycloalkyl; $R_1$ and $R_2$ represent hydrogen or lower alkyl; $R_3$ represents hydrogen or acyl; $R_4$ represents lower alkyl; or a pharmaceutically acceptable salt thereof provided that $R_3$ represents hydrogen.

6. A compound according to claim 5 wherein $R_3$ represents hydrogen; or a pharmaceutically acceptable salt thereof.

7. A compound according to claim 5 of the formula

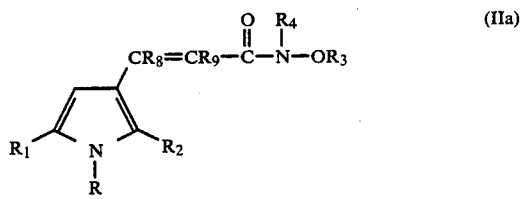

(IIa)

wherein R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represents hydrogen, methyl or ethyl; $R_8$ and $R_9$ independently represent hydrogen, methyl or ethyl; $R_3$ represents hydrogen; $R_4$ represents $C_1$–$C_3$-alkyl; or a pharmaceutically acceptable salt thereof.

8. A compound according to claim 1 of the formula

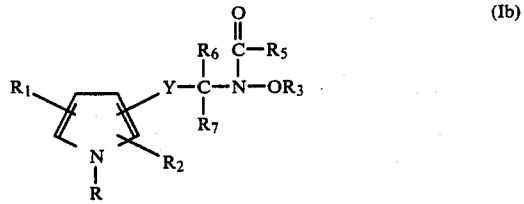

(Ib)

wherein Y represents a direct bond, lower alkylene, lower alkenylene or lower alkadienylene; R represents aryl, aryl-lower alkyl, cycloalkyl, bicycloalkyl or adamantyl; $R_1$ and $R_2$ represent hydrogen or lower alkyl; $R_3$ represents hydrogen or acyl; $R_5$ represents lower alkyl, $C_3$–$C_7$-cycloalkyl, aryl, aryl-lower alkyl, amino or N-(mono- or dialkyl)-amino; $R_6$ and $R_7$ represent hydrogen or lower alkyl; or a pharmaceutically acceptable salt thereof provided that $R_3$ represents hydrogen.

9. A compound according to claim 8 of formula Ib wherein Y represents a direct bond or lower alkenylene; R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono- or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represent hydrogen, methyl or ethyl; $R_3$ represents hydrogen, lower alkanoyl or aroyl; $R_5$ represents $C_1$–$C_3$-alkyl, amino or N-(mono- or di-lower alkyl)-amino; $R_6$ represents hydrogen; $R_7$ represents hydrogen or $C_1$–$C_3$ alkyl; or a pharmaceutically acceptable salt thereof provided that $R_3$ represents hydrogen.

10. A compound according to claim 9 of the formula

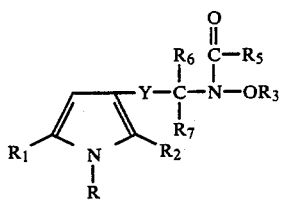

(III)

wherein Y, R, $R_1$–$R_3$ and $R_5$–$R_7$ have meanings as defined in said claim; or a pharmaceutically acceptable salt thereof provided that $R_3$ represents hydrogen.

11. A compound according to claim 10 wherein Y represents a direct bond.

12. A compound according to claim 10 wherein $R_3$ represents hydrogen.

13. A compound according to claim 10 of the formula

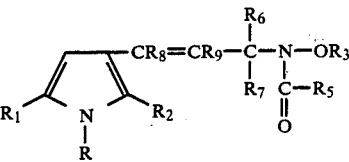

(IIIa)

wherein R represents aryl or aryl-lower alkyl in which aryl represents phenyl or phenyl substituted by one, two or three radicals selected from lower alkyl and halogen, or aryl represents phenyl substituted by a cyano, carbamoyl or N-(mono or di-lower alkyl)-carbamoyl radical; or R represents cyclopentyl, cyclohexyl or cycloheptyl; or R represents unsubstituted or lower alkyl-substituted bicyclo[2,2,1]heptyl; $R_1$ and $R_2$ represents hydrogen, methyl or ethyl; $R_3$ represents hydrogen; lower alkanoyl or aroyl; $R_5$ represents $C_1$–$C_3$-alkyl, amine or N-(mono or di-lower alkyl)-amino; $R_6$ represents hydrogen; $R_7$, $R_8$ and $R_9$ represent hydrogen or $C_1$–$C_3$-alkyl; or a pharmaceutically acceptable salt thereof provided that $R_3$ represents hydrogen.

14. A compound according to claim 7 being (E)-3-(1-cycloheptyl-1H-pyrrol-3-yl)-N-hydroxy-N-methyl-2-propenamide or a pharmaceutically acceptable salt thereof.

15. A compound according to claim 7 being (E)-3-[1-(2-norbornanyl)-1H-pyrrol-3-yl]-N-hydroxy-N-methyl-2-propenamide or a pharmaceutically acceptable salt thereof.

16. A pharmaceutical composition suitable for inhibiting 5-lipoxygenase activity in mammals comprising an effective 5-lipoxygenase inhibiting amount of a compound of claim 1 in combination with one or more pharmaceutically acceptable carriers.

17. A method of inhibiting lipoxygenase activity and of treating disorders in mammals which are responsive to such inhibition which comprises administering to a mammal in need thereof an effective lipoxygenase inhibiting amount of a compound of claim 1 or of a said compound in combination with one or more pharmaceutically acceptable carriers.

18. A method of inhibiting lipoxygenase activity and of treating disorders in mammals which are responsive to such inhibition which comprises administering to a mammal in need thereof an effective lipoxygenase inhibiting amount of a compound of claim 7 or of a said compound in combination with one or more pharmaceutically acceptable carriers.

* * * * *